(12) United States Patent
Evans

(10) Patent No.: US 8,627,516 B2
(45) Date of Patent: Jan. 14, 2014

(54) REMOVABLE BAND FOR VISOR

(75) Inventor: Lynn Evans, Anaheim Hills, CA (US)

(73) Assignee: Mixm, Inc., Anaheim Hills, CA (US)

( * ) Notice: Subject to any disclaimer, the term of this patent is extended or adjusted under 35 U.S.C. 154(b) by 118 days.

(21) Appl. No.: 13/092,483

(22) Filed: Apr. 22, 2011

(65) Prior Publication Data

US 2012/0210493 A1 Aug. 23, 2012

Related U.S. Application Data

(60) Provisional application No. 61/444,349, filed on Feb. 18, 2011.

(51) Int. Cl.
*A42B 1/00* (2006.01)
*A41D 27/08* (2006.01)

(52) U.S. Cl.
USPC ............................................. 2/175.1; 2/244

(58) Field of Classification Search
USPC ............... 2/181, 175.3, 209.11, 209.13, 244, 2/175.1
See application file for complete search history.

(56) References Cited

U.S. PATENT DOCUMENTS

| 993,257 | A | * | 5/1911 | Kopp | 2/175.3 |
|---|---|---|---|---|---|
| 1,490,565 | A | * | 4/1924 | Hunter | 40/329 |
| 1,640,895 | A | * | 8/1927 | Hills | 2/175.3 |
| 1,643,335 | A | * | 9/1927 | Dootson | 2/175.3 |
| 1,646,153 | A | * | 10/1927 | Kreh | 2/175.3 |
| 1,653,732 | A | * | 12/1927 | Roberts | 2/175.3 |
| 1,773,514 | A | * | 8/1930 | Brenner | 2/175.3 |
| 1,791,556 | A | * | 2/1931 | Chemidlin | 24/710.5 |
| 1,793,386 | A | * | 2/1931 | Cavanagh | 24/710.5 |
| 1,811,187 | A | * | 6/1931 | Roberts | 24/710.5 |
| 1,869,801 | A | * | 8/1932 | Donato | 2/175.3 |
| 1,928,019 | A | * | 9/1933 | Hock | 2/175.3 |
| 2,043,330 | A | * | 6/1936 | Nelkin | 2/175.3 |
| 2,048,425 | A | * | 7/1936 | Caplain | 2/175.3 |
| 2,068,760 | A | * | 1/1937 | Olson | 2/175.3 |
| 2,166,337 | A | * | 7/1939 | Bauwens | 2/175.3 |
| 2,440,407 | A | * | 4/1948 | Kuenstner | 2/175.3 |
| 2,445,922 | A | * | 7/1948 | Ostolaza et al. | 2/175.3 |
| 2,491,183 | A | * | 12/1949 | Jones | 2/175.3 |
| 2,509,490 | A | * | 5/1950 | Fecteau | 43/57.1 |
| 2,579,558 | A | * | 12/1951 | Fine | 24/179 |
| 2,580,323 | A | * | 12/1951 | Russell | 2/181 |
| 2,597,601 | A | * | 5/1952 | Sherman | 43/57.1 |
| 2,769,272 | A | * | 11/1956 | Goldman | 446/27 |
| 3,206,766 | A | * | 9/1965 | Smith | 2/209.7 |
| 4,630,317 | A | * | 12/1986 | Brown et al. | 2/12 |
| 5,369,808 | A | * | 12/1994 | Brewer et al. | 2/175.3 |
| 5,410,761 | A | | 5/1995 | Connelly et al. | |
| 5,477,629 | A | | 12/1995 | Gleason, Jr. | |
| 5,509,144 | A | | 4/1996 | Soergel et al. | |
| 5,561,864 | A | * | 10/1996 | DeMars | 2/209.13 |

(Continued)

OTHER PUBLICATIONS

"Visor Versa." Retrieved from the internet on Feb. 15, 2011. URL: https://www.visorversa.com.

*Primary Examiner* — Amber Anderson
(74) *Attorney, Agent, or Firm* — Stine Law Ltd.

(57) ABSTRACT

A removable band for a conventional sun visor is disclosed. The removable band allows a visor-wearer to customize their visor without having to permanently alter their visor. A non-damaging adhesive may be used to affix the removable band to the visor and may be reused multiple times. The removable band may have decorative elements such as colors, patterns, themes, logos, lettering, attachments, rhinestones or other attractive decorations.

3 Claims, 12 Drawing Sheets

(56) References Cited

U.S. PATENT DOCUMENTS

| | | | |
|---|---|---|---|
| 5,649,327 A * | 7/1997 | Crewe | 2/172 |
| 5,659,896 A * | 8/1997 | Taylor | 2/12 |
| 5,701,607 A | 12/1997 | Kaiser | |
| D415,605 S * | 10/1999 | Ae | D2/876 |
| 5,996,116 A * | 12/1999 | Tate | 2/12 |
| 6,009,555 A * | 1/2000 | Siprut | 2/12 |
| 6,029,272 A * | 2/2000 | Bazin | 2/12 |
| 6,175,963 B1 | 1/2001 | Loeffelholz | |
| 6,230,332 B1 * | 5/2001 | Gonzales | 2/209.13 |
| 6,279,168 B1 * | 8/2001 | Bean | 2/209.13 |
| 6,385,776 B2 * | 5/2002 | Linday | 2/171.1 |
| 6,463,592 B1 * | 10/2002 | Brooks | 2/209.12 |
| 6,643,847 B1 | 11/2003 | Dornak | |
| 6,738,985 B2 * | 5/2004 | Hahn et al. | 2/181 |
| 2010/0162464 A1 * | 7/2010 | Beard | 2/175.3 |
| 2010/0277944 A1 * | 11/2010 | Hurwitz | 362/570 |
| 2012/0180193 A1 * | 7/2012 | Curiel | 2/209.11 |
| 2012/0185996 A1 * | 7/2012 | Goldberg et al. | 2/160 |

* cited by examiner

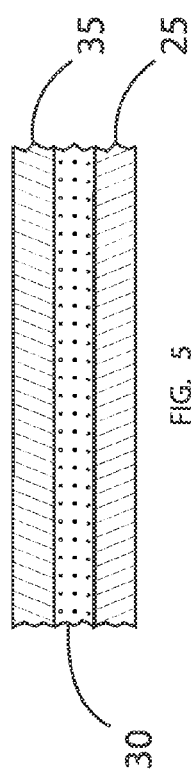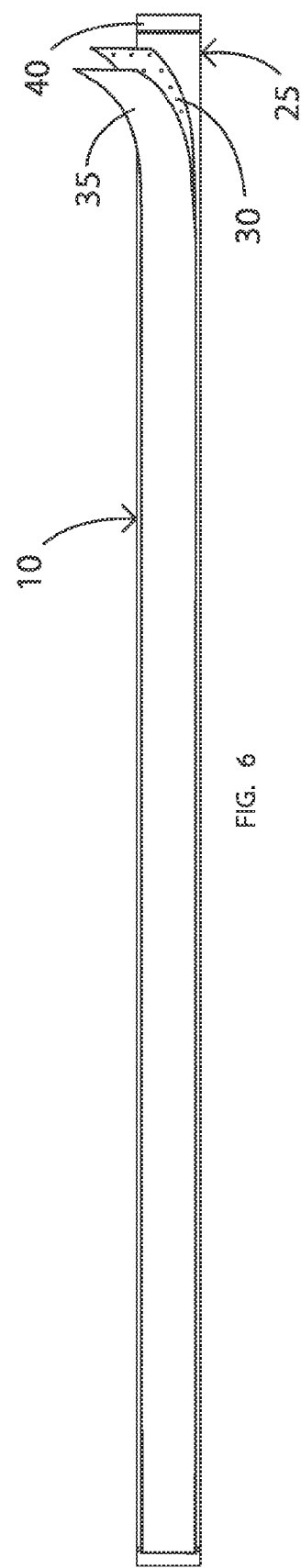

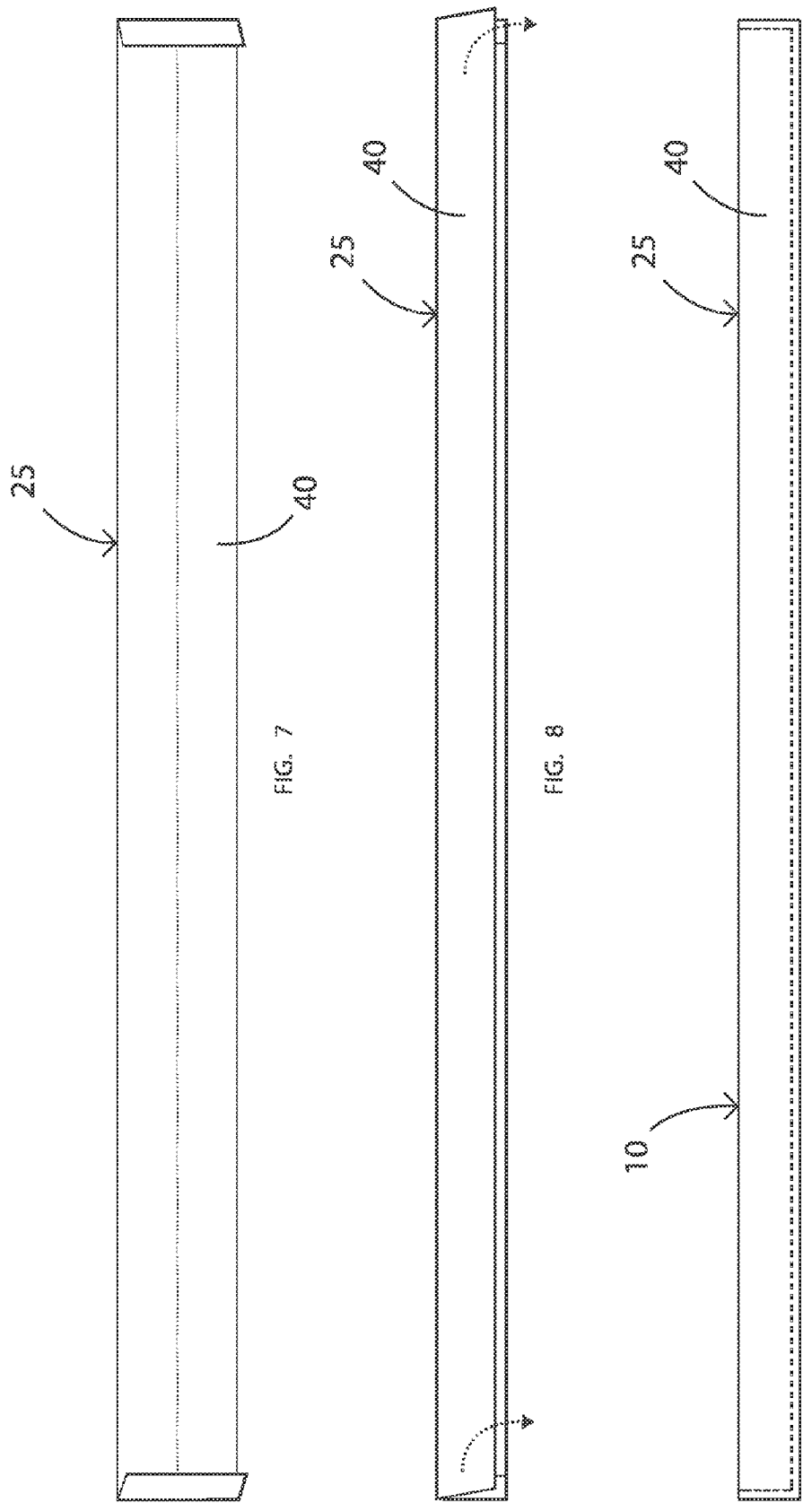

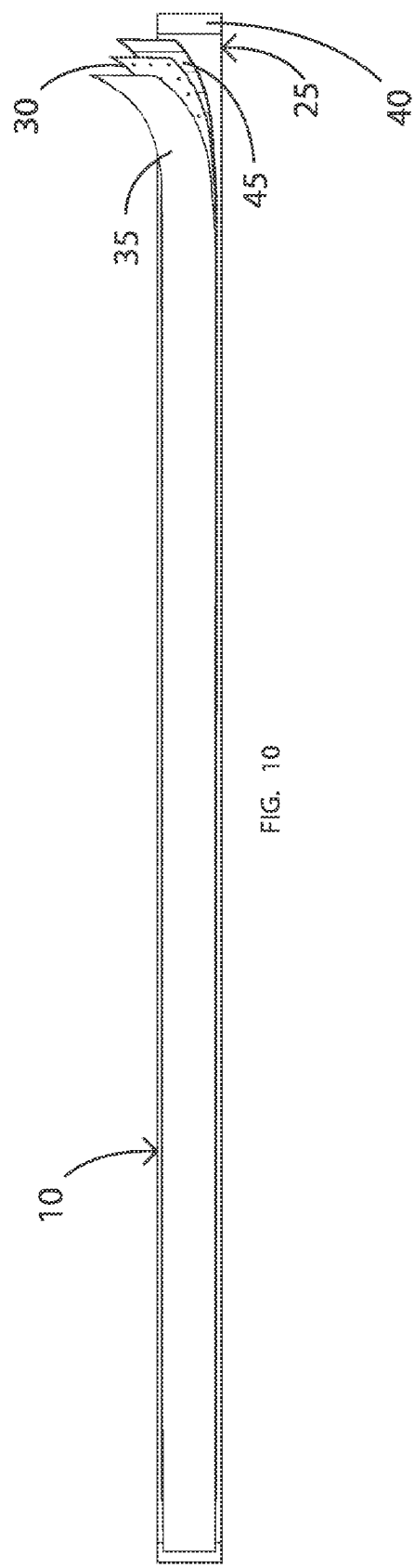

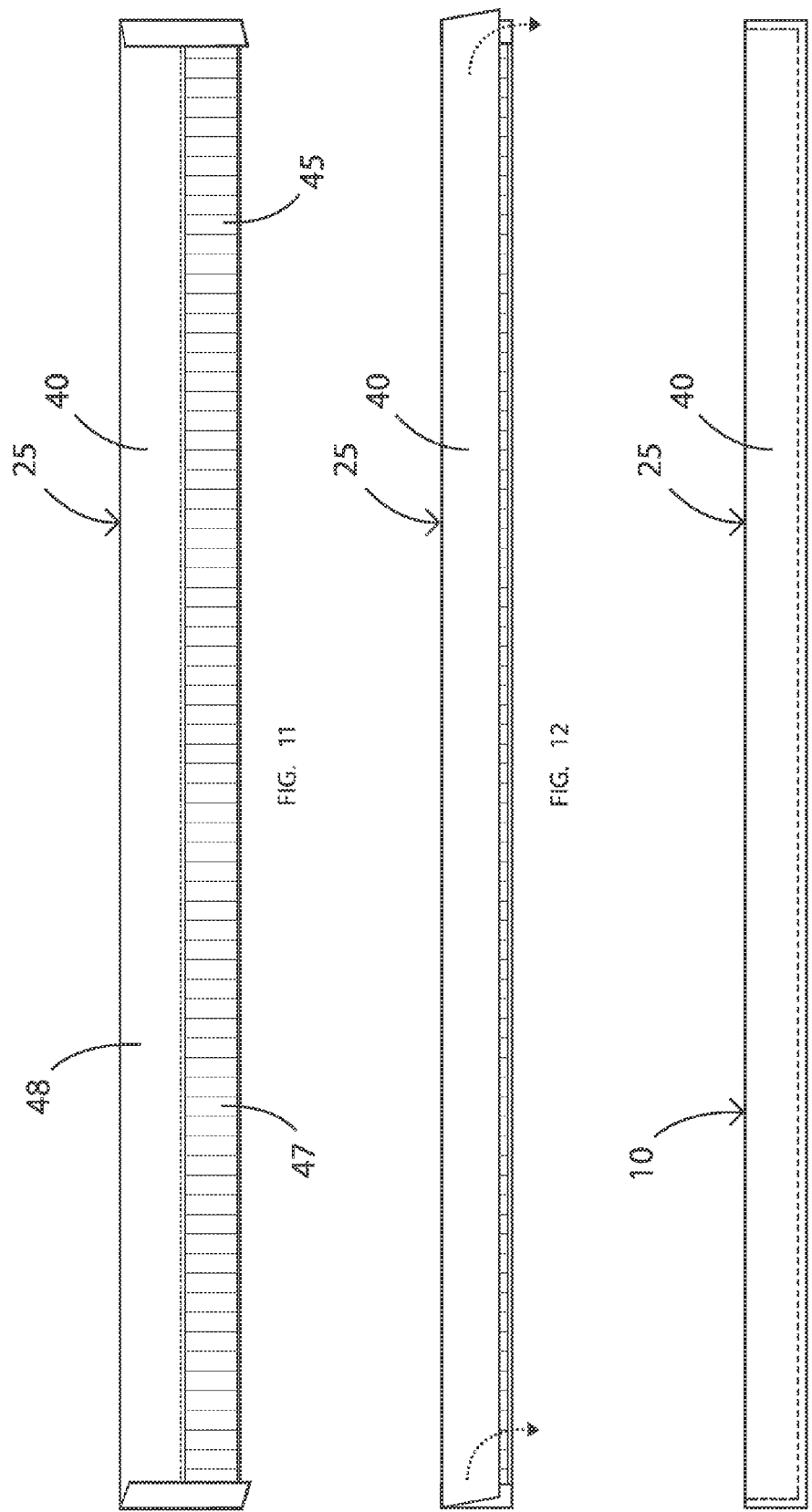

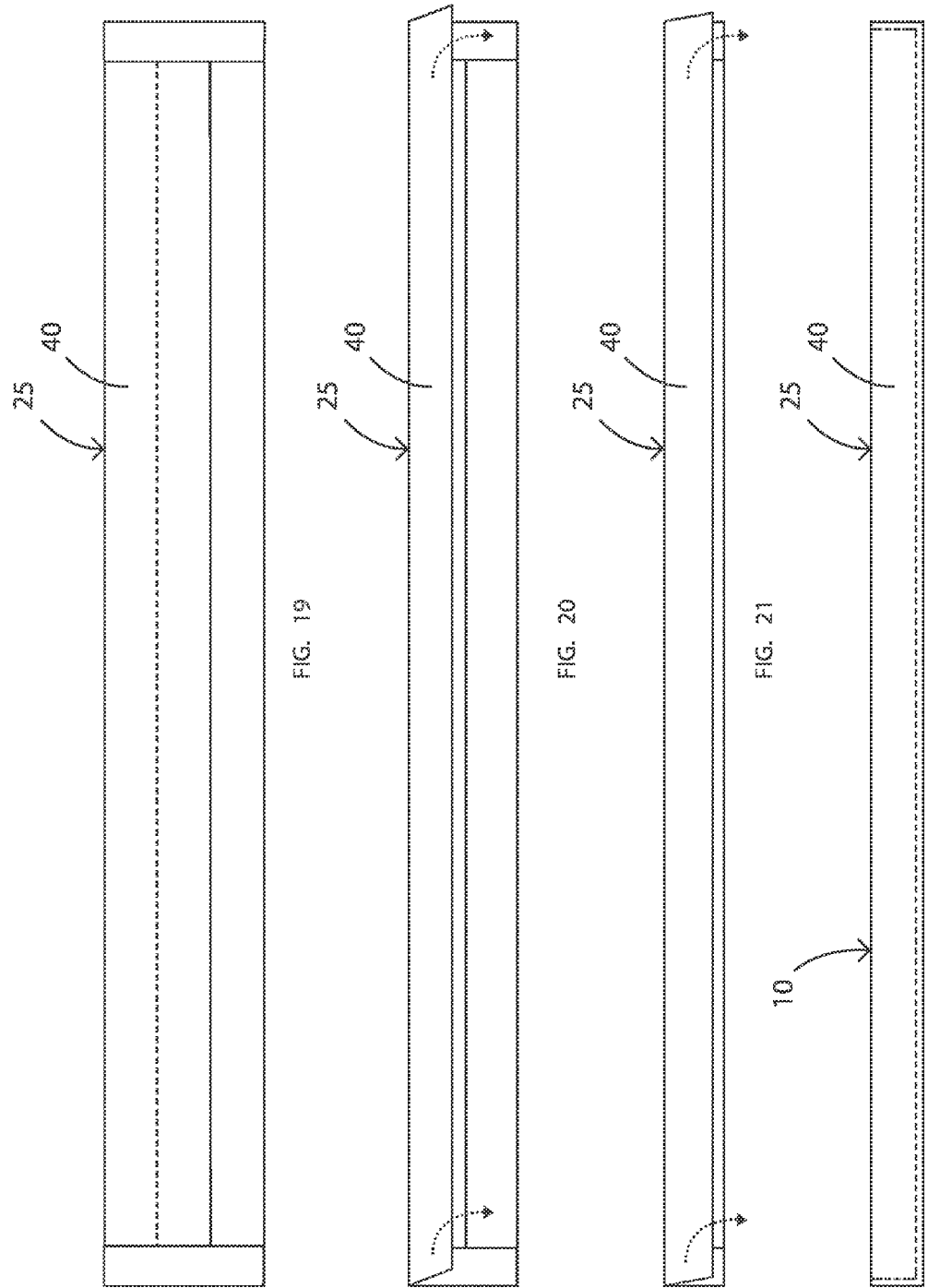

REMOVABLE BAND FOR VISOR

CROSS-REFERENCE TO RELATED APPLICATIONS

The present application claims the benefit of provisional application No. 61/444,349, filed in the United States Patent Office on Feb. 18, 2011.

TECHNICAL FIELD

This invention relates to headwear, and more particularly, to sun visors.

BACKGROUND OF THE ART

The sun visor, or simply "visor," is a popular form of headwear. A visor typically has a bill that protrudes forward from the head when worn and semi-rigid side arms that grip the head of the wearer to keep the visor in place. The bill of the visor provides shade on the face of the wearer, blocking the sun from the eyes of the wearer.

The visor is an alternative to baseball-style hats and offers several advantages. One advantage of the visor is that it is open on top, providing ventilation and allowing the wearer to wear a variety of hair styles that would ordinarily not be possible while wearing a baseball-style hat.

Visors are typically available in one head size; however they are available in a wide variety of colors and patterns and in at least two different bill sizes. Visors may be purchased having a variety of decorative elements, such as solid colors, patterns, beading, animal skin patterns, rhinestones, lettering, logos and the like. The cost of a visor often depends on the number and type of decorative elements, with more decorative visors costing more than plain or undecorated visors.

U.S. Pat. No. 6,643,847 to Dornak discloses a baseball cap that allows for the personalized placement of multiple logos, insignias, or text. The cap contains multiple pockets for the placement of team logos, player names, manufacturers' logos, text, pictures and the like. However, the hat must have specially adapted pockets to receive the decorative elements.

U.S. Pat. No. 5,477,629 to Gleason discloses a multi-adjustable display cap that includes a head covering with a display region of fabric conducive to releasable engagement with a hook element of a hook-and-loop type fastener. However, the hat must have an area adapted to receive and engage the hooks of a hook and loop fastening system.

U.S. Pat. No. 5,410,761 to Connelly discloses a cap having a visor with diverse pictorial displays placed on an insert that is located on the top surface of the visor, the insert being protected by a plastic envelope fastened to the visor with a strip of hook and loop material. However, the decorative elements must be inserted in a specially adapted plastic envelope.

U.S. Pat. No. 5,509,144 to Soergel discloses a baseball cap configured to permit different logos to be interchangeably positioned on the cap. The two panels defining the front face of the cap are made out of pile material and other panels of the crown portion, as well as the visor, can also be made out of pile material. The logos are equipped with hook fastener material which permits them to be detachably mounted on the cap. However, the hat must have an area adapted to receive and engage the hooks of a hook and loop fastening system.

U.S. Pat. No. 6,175,963 to Loeffelholz discloses a system and method for detachably securing emblems, or the like, to articles of clothing, such as caps, hats, shirts, jackets, belts, and shoes. The system employs the combination of two magnetically attractive elements, for example, a magnet and a plate or a piece of ferromagnetic material. However, magnets must be used and a magnet placed between the visor and the wearer's head may cause discomfort.

U.S. Pat. No. 5,701,607 to Kaiser discloses an overlay for a cap bill or visor. The overlay is constructed of impermeable, flexible material. On the underside of the overlay is an adhesive covered by a protective film. This protective film is removed and the overlay is placed on top of the cap bill, and the adhesive holds the overlay in place. However, the overlay may only be placed on the bill of a cap or visor. In addition, the overlay has a crescent shape. Further, the overlay has a sheet material that is only somewhat flexible. The present system may be placed on the band area of a visor and is generally flexible. In addition, the present system gives the appearance of being a part of the visor and not an overlay.

A visor known as the "Visor Versa" is also known. It features a removable band that is attached to a visor using hook and loop fasteners. However, this requires a specially adapted visor.

SUMMARY

The apparatuses disclosed herein provide a removable band that can be added to a conventional sun visor and removed without need for a specialized visor or modifications to the visor. The band may contain any number or combination of decorative elements desirable to accessorize the visor.

One benefit of the removable band is that a number of looks and styles may be achieved with a single visor as different bands are placed on the visor. Thus the visor wearer would no longer have to buy different visors to go with different outfits or to be appropriate at different events or occasions. Accordingly the number of visors that a person must purchase is decreased. This cost savings is significant as certain fanciful visors may cost significantly more.

BRIEF DESCRIPTION OF THE DRAWINGS

FIG. 5 is a diagrammatic view of a section of the removable band of FIG. 1;

FIG. 6 illustrates the removable band of FIG. 1 made of a fabric;

FIGS. 7-9 illustrate the base layer of the removable band made of a folded fabric;

FIG. 10 illustrates the removable band made of a fabric and a structural element;

FIGS. 11-13 illustrate the base layer of the removable band made of a folded fabric and a structural element;

FIGS. 14-22 illustrate the base layer of the removable band made of a folded fabric and a structural element;

DETAILED DESCRIPTION OF THE PREFERRED EMBODIMENT

Figure 1:
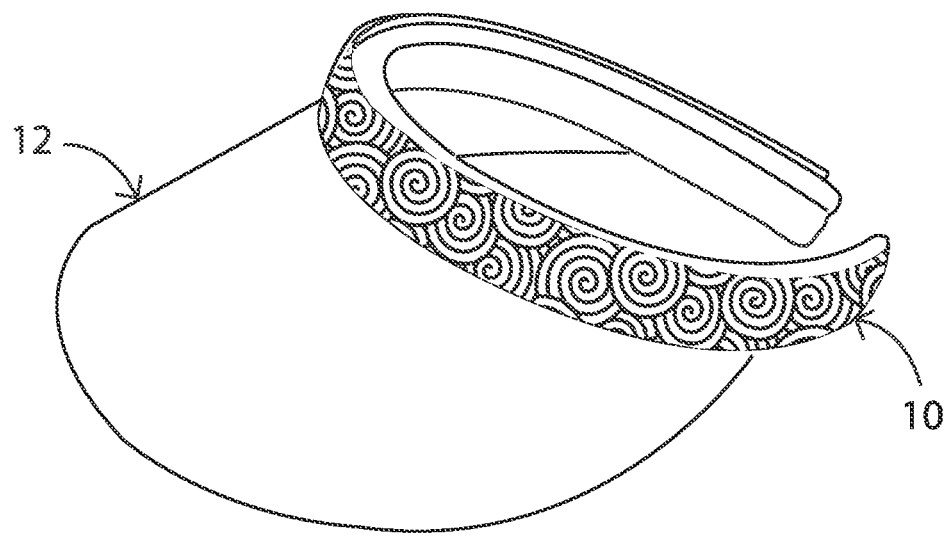
FIG. 1 is a perspective view of a removable band in accordance with the invention, shown affixed to a visor.

While this invention is susceptible of embodiments in many different forms, there is shown in the drawings and will herein by described in detail preferred embodiments of the invention with the understanding that the present disclosure is to be considered as an exemplification of the principles of the invention and is not intended to limit the broad aspect of the invention to the embodiments illustrated.

Figure 2:
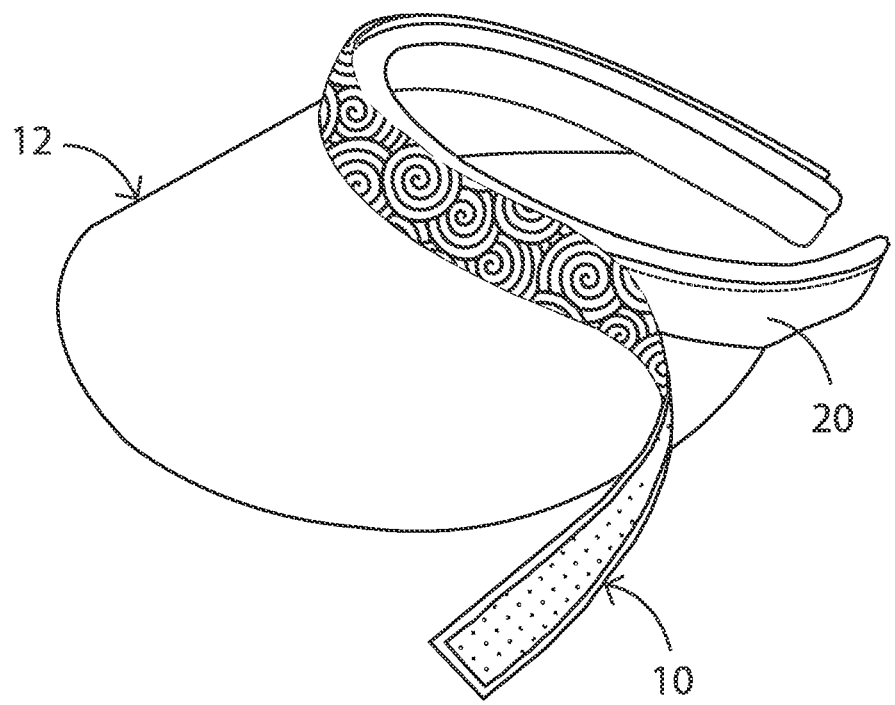
FIG. 2 is a perspective view of the removable band of FIG. 1 shown partially affixed to the visor.
Figure 3:
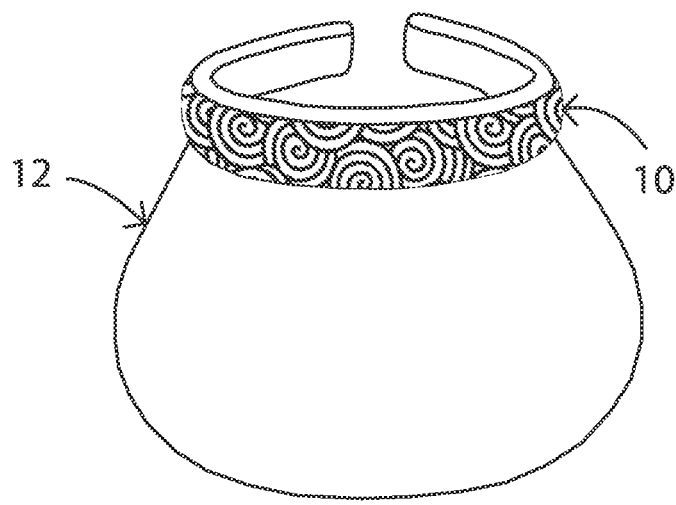
FIG. 3 is a front view of the removable band of FIG. 1 shown affixed to the visor.
Figure 4:
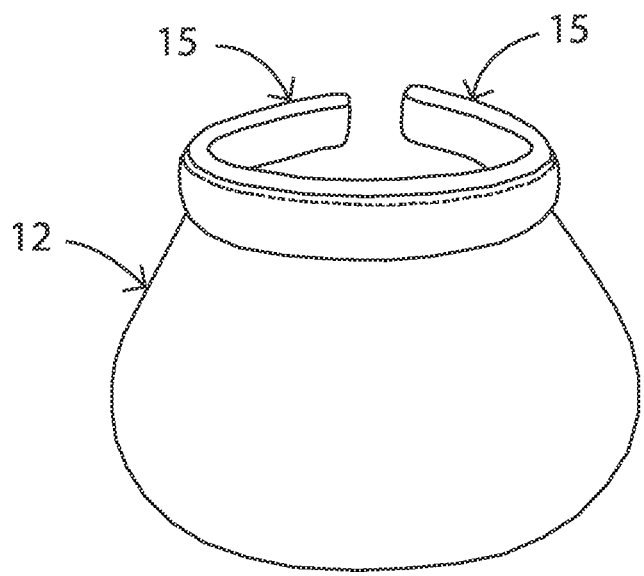
FIG. 4 is a front view of the visor without the removable band.

A removable band, generally designated 10 in combination with a visor 12, is illustrated in FIGS. 1-3. The visor 12 without the removable band 10 is shown in FIG. 4. The visor 12 may include side arms 15. The removable band 10 is placed on a band area 20 (or "crown") of the visor 12. The removable band 10 is not permanently affixed to the visor 12 and so may be removed without damaging the visor 12. The removable band 10 may contain any number or combination of decorative elements, including, without limitation, lettering, logos, designs, colors, patterns, shapes, textures, beads, rhinestones and the like. Thus without modifying the visor 12, the visor 12 can be decorated in a number of ways using different removable bands.

The removable band 10 may be formed by layers, as shown in FIG. 5: a base layer 25 and an adhesive layer 30. Alternatively, a protective layer 35 may be adjoined to the adhesive layer 30. The protective layer 35 would be removed, exposing the adhesive layer 30, prior to attachment of the band 10 to the visor 12.

As used herein, the term "fabric" refers to any variety of cloth, ribbon or the like. Fabric may be cotton, polyester, felt, linen, or any material made of natural, artificial, or synthetic fibers or the like. Fabric includes leather or any material that may be used to create clothing. Fabric may also be any printed matter, including paper.

The base layer 25 may be constructed with a variety of materials and in a variety of configurations. The base layer 25 may be non-rigid and may be the same dimensions as the band area 20 of the visor 12.

According to one embodiment, the base layer 25 may be made of a fabric 40, as shown in FIG. 6.

According to another embodiment, the base layer 25 may be made of the fabric 40 folded on itself along its longitudinal axis, as shown in FIGS. 7-9. The folded fabric 40 may be stitched as shown in FIG. 9. Alternatively, an adhesive may be used to affix the folded fabric to itself.

According to another embodiment, the base layer 25 may be made of two layers: the fabric 40 and a structural element 45 as shown in FIG. 10. The structural element 45 may be rubber, elastic, cardboard, paper, tape, vinyl or the like. For example, the structural element 45 may be a braided elastic, such as Dritz® brand ¾ inch Braided Elastic. Many materials would be too thick to be structural elements as they would protrude too far from the visor and would create an unattractive appearance. For example, some rubber materials were found to be too thick. The structural element 45 gives form and/or strength to the removable band 10 while remaining flexible. The structural element 45 is found between the adhesive layer 30 and the layer of fabric 40.

According to another embodiment, the base layer 25 may be made of the fabric 40 folded over and enclosing the structural element 45 as shown in FIGS. 11-13. For example, an elastic strip 47 may be placed on a ribbon 48 that is of sufficient dimensions such that when the ribbon 48 is folded along its longitudinal axis, the ribbon 48 encloses, either partially or fully, the elastic strip 47. The longitudinal ends of the ribbon 48 may be folded over the elastic strip 47 if the ribbon 48 is longer than the elastic strip 47 as shown in FIG. 11. The elastic strip 47 may be affixed to the ribbon 48 by adhesive. Once folded, the ribbon 48 may be stitched around some or all of its borders as shown in FIG. 13. Alternatively, an adhesive may be used to affix the folded ribbon to itself.

Figure 14:
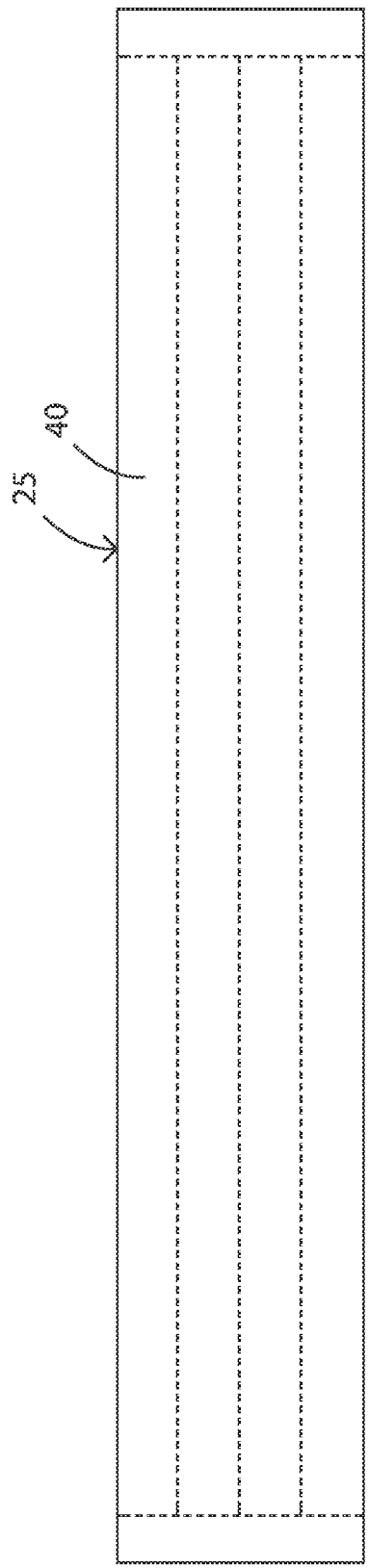
Figure 15:
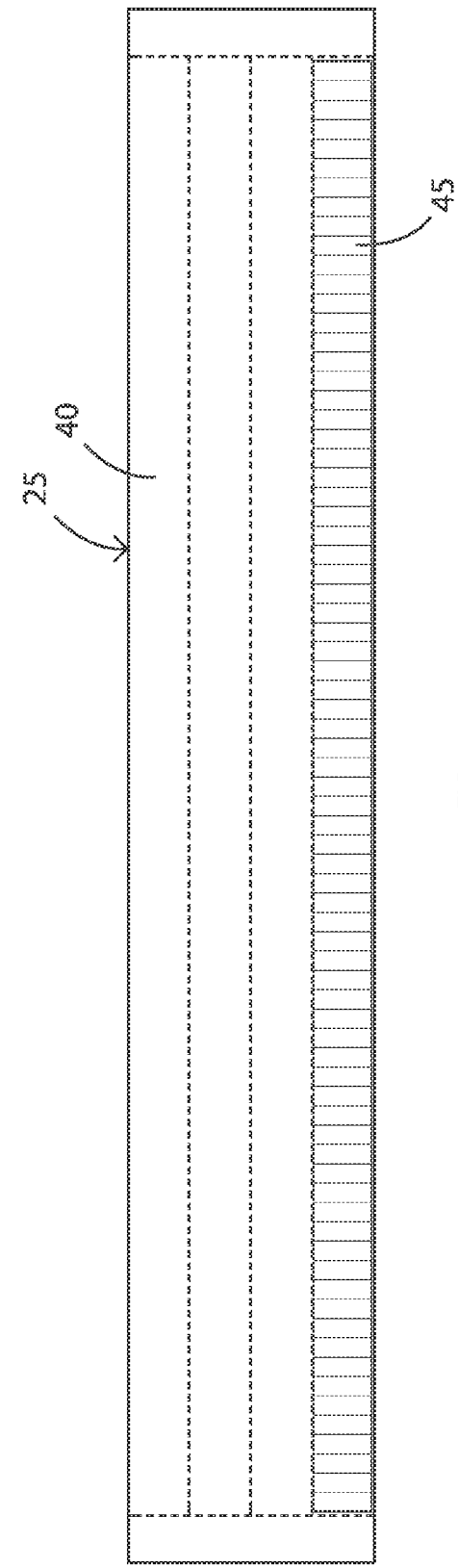
Figure 16:
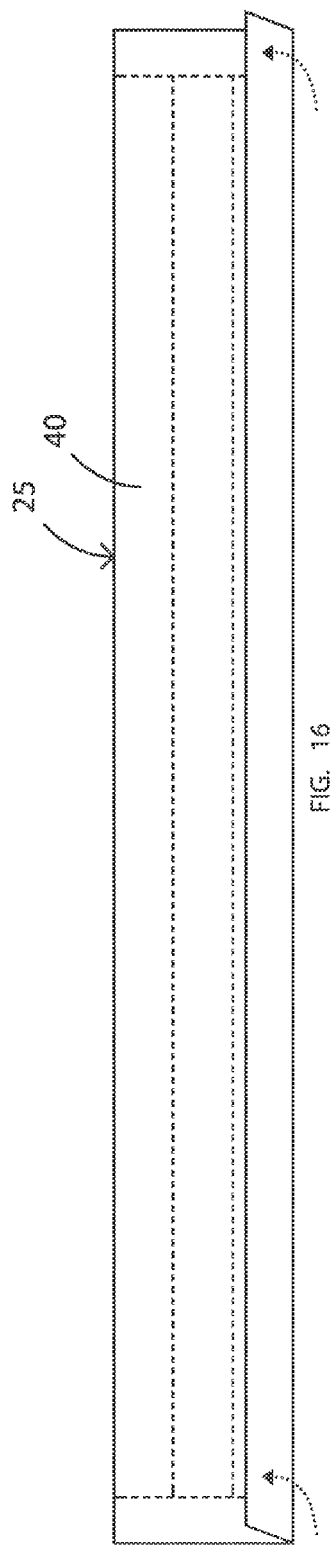
Figure 17:
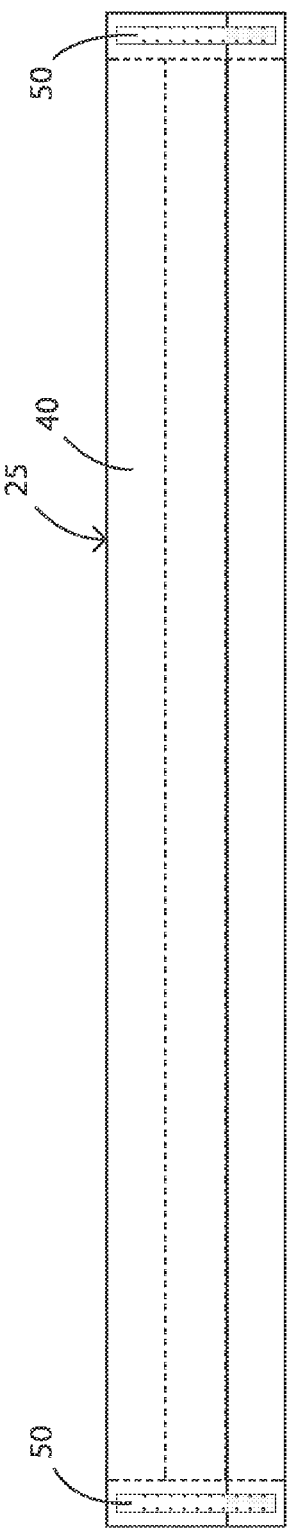
Figure 18:
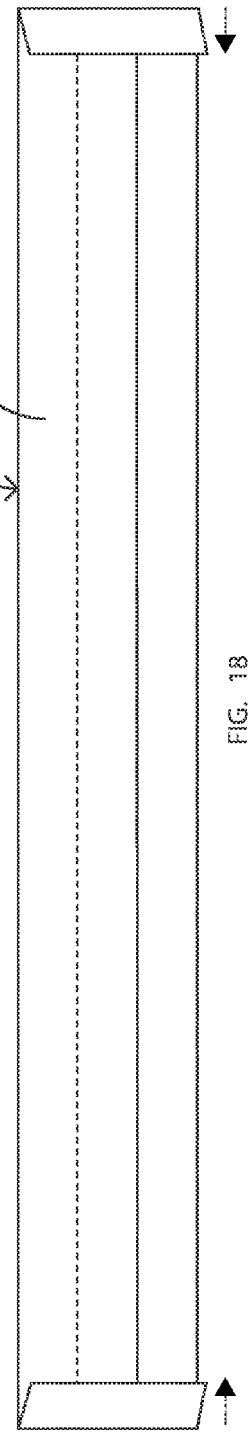

According to another embodiment, the fabric 40 is folded multiple times to create desired dimensions, and the structural element 45 may be enclosed within as shown in FIGS. 14-22. For example, if the desired size of the removable band 10 is 17¾"×¾", the fabric 40 measuring 18¾"×3" may be used as shown in FIG. 14. The structural element 45 is first centered horizontally along the bottom longitudinal edge of the fabric 40 as shown in FIG. 15. The structural element 45, along with the bottom ¾" of the fabric 40 is folded upward as shown in FIG. 16. An adhesive 50 may be placed on the longitudinal ends of the fabric 40 where the structural element 45 is not found as shown in FIG. 17. The longitudinal end of the fabric 40 may be folded in if the fabric 40 is longer than the structural element 45 as shown in FIG. 18. The top ¾" of the fabric 40 may then be folded down as shown in FIG. 20. Finally, the fabric 40 may be folded in half along its longitudinal axis, producing a finished base layer 25 that is roughly 17¾"×¾" as shown in FIGS. 21-22. Some or all of the borders of the fabric 40 may be stitched together as shown in FIG. 22. Alternatively, an adhesive may be used to affix the folded fabric 40 to itself.

The adhesive layer 30 may be any adhesive that is reusable and does not damage the visor. Accordingly the adhesive retains its stickiness despite multiple uses and does not leave behind noticeable residue on the visor. An example of such an adhesive is the Dritz® brand Res-Q-Tape, sold by Prym Consumer USA Inc.

The protective layer 35 may be any material that will protect the adhesive layer 30 from unwanted affixation. For example, the protective layer 35 may be plastic or paper, such as the backing found on the Dritz® brand Res-Q-Tape. The protective layer 35 may be placed on the removable band 10 when the removable band 10 is not in use.

The decorative side of the base layer 25 is the side not disposed toward the adhesive layer 30. The decorative side may contain one or more decorative elements.

Figure 23:
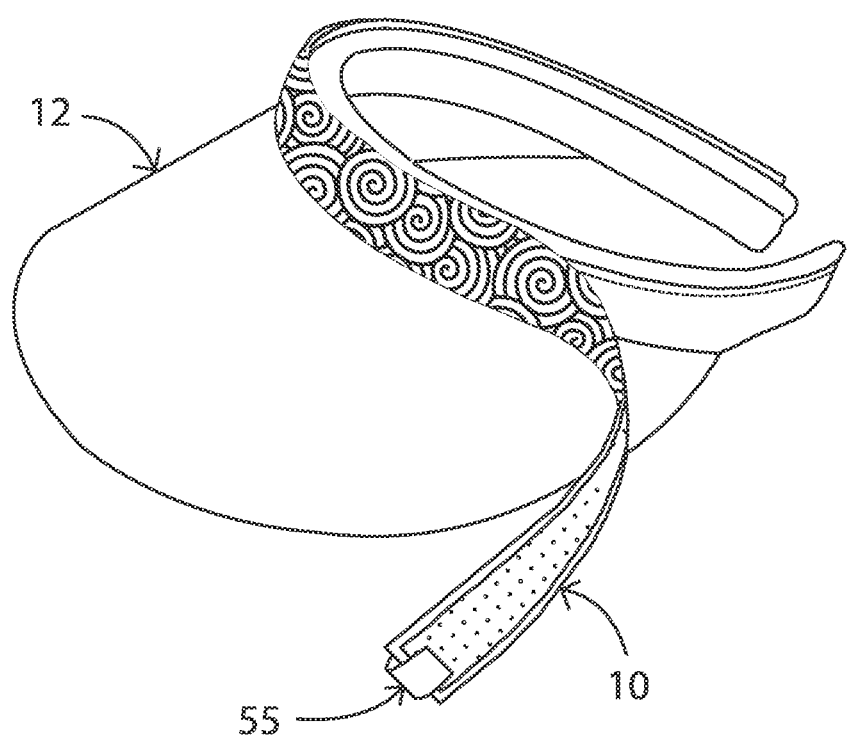
FIG. 23 illustrates the removable band with a clip assembly.
Figure 24:
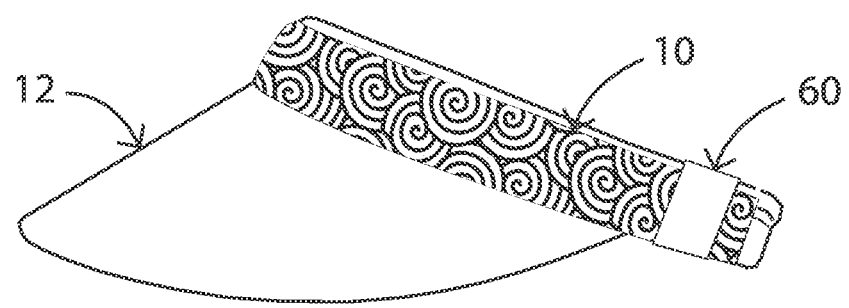
FIG. 24 illustrates the removable band held to the visor by an elastic member.
Figure 25:
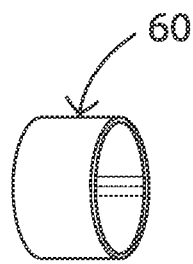
FIG. 25 illustrates the elastic member of FIG. 24.
Figure 27:
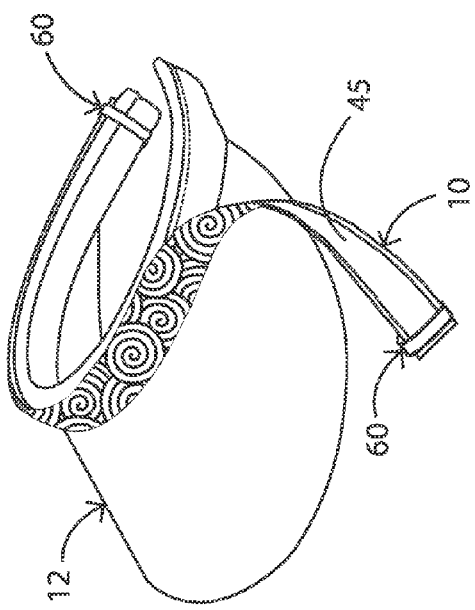
FIG. 27 illustrates the removable band of FIG. 26 partially secured to the visor by an elastic member.
Figure 26:
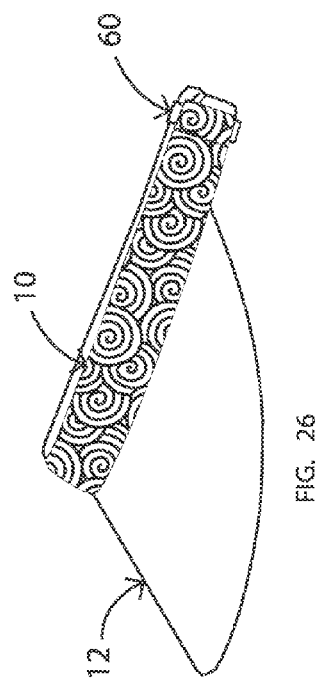
FIG. 26 illustrates a removable band secured to a visor by an elastic member.
Figure 28:
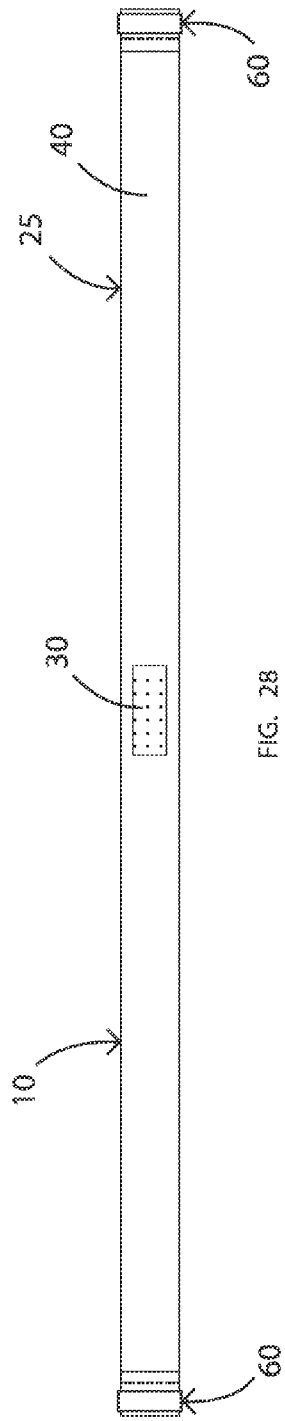
FIG. 28 illustrates a removable band with an adhesive.

According to another embodiment, the longitudinal ends of the removable band 10 are adapted to wrap around the side arms 15 of the visor, as shown in FIG. 23. In this embodiment, the removable band 10 is held in place principally by the connection to the side arms 15. The adhesive layer 30 may be present. The adhesive layer 30 may be shorter than the removable band 10 and may be disposed on the center of the removable band 10. The adhesive layer 30 on this embodiment helps to keep the removable band 10 in place on the visor. As an example of how the removable band 10 may wrap around the side arms, the removable band 10 may have an inward-facing pocket into which the end of the side arm 15 is placed. Alternatively, a clip 55 is disposed at the longitudinal ends of the removable band 10. Each of the clips 55 may be clipped onto the side arms 15. The clips 55 may be made of plastic, metal or the like. Importantly, the clips 55 should be thin so that the clips 55 do not protrude into the head of the wearer, causing possible discomfort or headache.

According to another embodiment, the longitudinal ends of the removable band 10 may be held in place by an elastic member 60 that wraps around both the side arms 15 and the removable band 10, as shown in FIGS. 24-28. The elastic member 60 may be separate from, or a part of, the removable band 10. The elastic member 60 may be disposed between folded layers of the fabric 40 or between other layers of the removable band 10 generally. The elastic member 60 may be affixed to the removable band 10 by adhesive, stitching, metal fasteners or the like. The elastic member 60 may be made of rubber, elastic or any other material that would stretch to fit around, and hold together, both the side arm 15 and the removable band 10. For example, the elastic member 60 may be made of Dritz® brand ¼ inch Braided Elastic. The adhesive layer 30 may be present. The adhesive layer 30 may be shorter than the removable band 10 and may be disposed on the center of the removable band 10. The adhesive layer 30 on this embodiment helps to keep the removable band 10 in place on the visor.

Alternatively, the removable band 10 may be used on a conventional ladies' headband instead of a visor. The dimensions of a headband are different than those of a visor and so a particular removable band may not be operable on both a headband and a visor.

While specific embodiments have been illustrated and described, numerous modifications may come to mind without significantly departing from the spirit of the invention, and the scope of protection is only limited by the scope of the accompanying claims.

The invention claimed is:

1. A method of customizing a visor comprising:
providing a visor including a band area, the band area having a length comprising a crown and opposing, non-engaging side arms extending from the crown, the band area having an inner side and an opposing outer side, the inner surface of the band area adapted to engage the wearer's head;
providing a removable band, the removable band comprising a base layer having an inner surface, an outer surface, two substantially parallel lateral edges, a top edge, and a bottom edge; the removable band formed by the inner surface having an adhesive attached thereto and the two lateral edges being folded over to adhere to the adhesive, the base layer is then folded in half substantially along a longitudinal axis and being affixed in the folded position and only having the outer surface visible, the removable band in the folded state has a front face and a rear face, the rear face having an adhesive strip attached thereto and the front face having at least one decorative element thereon;
the adhesive strip on the rear face of the removable band affixes the removable band to the outer side of the band area of the visor absent a cooperating adhesive layer on the band area of the visor, the removable band extending substantially along the length of the band area of the visor.

2. The method of claim 1 wherein the removable band is fabric.

3. The method of claim 1 wherein the removable band includes a structural element fabric.

* * * * *